(12) United States Patent
Reichow et al.

(10) Patent No.: US 8,430,547 B2
(45) Date of Patent: Apr. 30, 2013

(54) COMPACT MOTION-SIMULATING DEVICE

(75) Inventors: Alan W. Reichow, Beaverton, OR (US);
Herb Yoo, Beaverton, OR (US); Ryan C. Coulter, Portland, OR (US);
Christian Freissler, Portland, OR (US);
Dave R. Knaub, Portland, OR (US);
Meral Middleton, Portland, OR (US);
David Thorpe, Portland, OR (US); Tom Lakovic, Portland, OR (US); Andrew Allen, Seattle, WA (US); Josh Hoyt, Portland, OR (US)

(73) Assignee: Nike, Inc., Beaverton, OR (US)

( * ) Notice: Subject to any disclaimer, the term of this patent is extended or adjusted under 35 U.S.C. 154(b) by 803 days.

(21) Appl. No.: 12/534,598

(22) Filed: Aug. 3, 2009

(65) Prior Publication Data

US 2011/0028800 A1   Feb. 3, 2011

(51) Int. Cl.
*F21V 99/00* (2006.01)
(52) U.S. Cl.
USPC ........ 362/559; 362/85; 362/225; 362/249.02; 362/297; 362/247; 362/217.05; 362/800
(58) Field of Classification Search .................. 362/559, 362/85, 225, 249.02, 242, 341, 297, 247, 362/217.05; 315/323; 600/300; 446/485, 446/175, 219, 484; 353/94
See application file for complete search history.

(56) References Cited

U.S. PATENT DOCUMENTS

| | | |
|---|---|---|
| 3,861,790 A | 1/1975 | Tamura |
| 4,298,916 A | 11/1981 | Shemitz |
| 4,461,477 A | 7/1984 | Stewart |
| 4,702,475 A | 10/1987 | Elstein |
| 4,824,237 A | 4/1989 | Ratner |
| 5,050,982 A | 9/1991 | Meissner |
| 5,478,239 A | 12/1995 | Fuerst |
| 6,410,835 B2 | 6/2002 | Suzuki |
| 6,652,102 B2 | 11/2003 | Hayashi |

(Continued)

FOREIGN PATENT DOCUMENTS

WO   2006034543   4/2006

OTHER PUBLICATIONS

Reichow, et al., "Introduction to Behavioral Optometry", Sports Vision, 1993, 75 pages, Optometric Extension Program Foundation, United States.

(Continued)

*Primary Examiner* — Jong-Suk (James) Lee
*Assistant Examiner* — Leah S Macchiarolo
(74) *Attorney, Agent, or Firm* — Shook, Hardy & Bacon L.L.P.

(57) ABSTRACT

A reaction-testing system is provided to simulate motion to an individual. Generally, the reaction-testing system includes a motion-simulating device, a reflective device, a control unit, and an input device that is activated by an individual In exemplary embodiments, the motion-simulating device includes a beam that accommodates a first and second plurality of light sources capable of, at least, alternating between an active and idle condition. These light sources are arranged amongst occlusion features in a mounting pattern such that light emitted from the first plurality is directly viewable by an individual and light emitted from the second plurality is indirectly viewed by the individual through the reflecting surface. The control unit is configured to sequentially activate the light sources sequentially to generate pulses of light on that, when perceived by the individual, appear as a light moving along a vector.

13 Claims, 5 Drawing Sheets

U.S. PATENT DOCUMENTS

| | | |
|---|---|---|
| 6,755,525 B2 | 6/2004 | Reichow |
| 6,811,258 B1 | 11/2004 | Grant |
| 6,814,459 B2 | 11/2004 | Pederson |
| 6,893,127 B2 | 5/2005 | Reichow |
| 7,073,208 B2 | 7/2006 | Penque |
| 7,083,284 B2 | 8/2006 | Peterson |
| 7,353,071 B2 | 4/2008 | Blackwell |
| 7,380,791 B2 | 6/2008 | Gauselmann |
| 7,492,523 B2 | 2/2009 | Dolgoff |
| 8,070,325 B2 * | 12/2011 | Zampini et al. ............... 362/294 |

OTHER PUBLICATIONS

Ferreira, "An Overview of Research in Sports Vision: its History and an Optometric Perspective", The South African Optometrist, Dec. 2003, pp. 142-149, vol. 62, No. 4, Auckland Park, South Africa.

Coffey, et al., "Visual Performance Enhancement in Sports Optometry", Sports Vision 1995, pp. 158-177, Butterworth-Heinermann, United States.

Cardall, "Contact Lenses in Sport: a General Overview", Optician, Jan. 13, 2006, pp. 22-25, vol. 231, No. 6034, United States.

Rouse, et al., "A Comparison Study of Dynamic Visual Acuity Between Athletes and Nonathletes", Journal of the American Optometric Association, Dec. 1988, pp. 946-950, vol. 59, No. 12, United States.

Koenig, "Practicing Perception: Eyes Can Be Trained to be More Effective", USA Today Baseball Weekly, 1996, 3 pages, United States.

Coffey, et al., "Optometric Evaluation of the Elite Athlete," Problems in Optometry, Mar. 1990, pp. 32-59, vol. 2, No. 1, United States.

Reichow, et al., "A Comparison of Contrast Sensitivity in Elite Athletes Versus a Normal Population", American Journal of Optometry and Physiological Optics, Dec. 15, 1986, vol. 63, No. 82, United States.

Farrow, et al., "An Investigation of the Effectiveness of Bolle's Competivision Sport-Glasses on Tennis Performance", Clinical and Experimental Optometry, Jul.-Aug. 2000, pp. 226-231, vol. 83, No. 4.

Herdman, et al., "Computerized Dynamic Visual Acuity Test in the Assessment of Vestibular Deficits", The American Journal of Otology, 1998, pp. 790-796, vol. 19, No. 6, United States.

Tian, et al., "Dynamic Visual Acuity During Transient and Sinusoidal Yaw Rotation in Normal Ulilaterally Vestibulopathic Humans", Experimental Brain Research, Feb. 8, 2001, pp. 12-25, vol. 137, Springer-Verlag, United States.

Reichow, et al., "Ultraviolet and Short Wavelength Visible Light Exposure: Why Ultraviolet Protection Alone is Not Adequate", Journal of Long-Term Effects of Medical Implants, 2006, pp. 315-325, vol. 16, No. 4, Begell House, Inc., United States.

International Search Report and Written Opinion for PCT/US2010/044251 filed Aug. 3, 2010.

* cited by examiner

COMPACT MOTION-SIMULATING DEVICE

CROSS-REFERENCE TO RELATED APPLICATIONS

Not applicable.

STATEMENT REGARDING FEDERALLY SPONSORED RESEARCH OR DEVELOPMENT

Not applicable.

TECHNICAL FIELD

The present invention relates generally to the evaluation and/or training of an individual's visual abilities.

BACKGROUND OF THE INVENTION

Numerous activities, particularly competitive athletics, place particularized demands upon the perceptive and reactive abilities of an individual. Accordingly, a variety of reactive evaluation exercises have been developed that may be performed upon the individual, or athlete, to test the strengths and weaknesses of the individual's visual, cognitive, and physical abilities. Typically, such testing techniques are applied to determine whether an individual may benefit from reaction-related training and may be utilized for training purposes.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

The present invention offers several practical applications in the technical arts, not limited to systems and methods for testing and/or training an individual's anticipation time. Systems in accordance with the present invention simulate dynamic movement over time. A motion-simulating device in accordance with the present invention may include a plurality of light sources, a reflective device, and a control unit. By sequentially activating light sources, systems in accordance with the present invention may simulate motion. Further, an input device that is activated by an individual when the individual anticipates a predetermined light source will be activated may be used in conjunction with embodiments of the present invention. In exemplary embodiments, the motion-simulating device includes a beam having a first and a second plurality of light sources capable of, at least, alternating between an active and idle condition. These light sources may be arranged such that light emitted from the first plurality of light sources is directly viewable by an individual but prevented from reaching the reflecting surface. Conversely, the second plurality of light sources may be occluded to prevent light from being directly viewed by the individual, but exposed in another direction to allow emitted light to reach the reflecting surface.

The control unit may sequentially activate one or more light sources of the second plurality of light sources and then sequentially activate one or more light sources of the first plurality of light sources. In one embodiment, sequentially activating includes recursively triggering one or more light sources to the cycle through the active condition based on test instructions executed by the control unit. Accordingly, the sequential actuation generates pulses of light on the stationary first and second plurality of light sources that, when perceived by the individual located at a particular position relative to the motion-simulating device, appear as a light moving along a vector. Further, the beam of the motion-simulating device may reside in an angular orientation with respect to the reflecting surface such that the individual perceives the simulated motion as originating from a distal location and moving towards a proximal location. Advantageously, the reflecting surface may be strategically placed to generate a visual perspective of distance within a limited spatial area.

During the process of sequential activation, the test instructions may serve to control which of the light sources are selected for activation and the duration of the cycle through the active condition of the selected light sources (i.e., the amount of time illumination is emitted from a particular light source).

In operation, when performing a test of an individual's perception, cognition, and/or reaction abilities in accordance with embodiments of the present invention, the individual may be prompted to engage the input device when the simulated motion encounters a predetermined position. The control unit may detect a time of the engagement and determine preciseness of the individual's response based on a comparison of the engagement time and an expected time (i.e., the time the simulated motion actually encounters the predetermined position on the vector). Alternatively, the distance (i.e., number of light sources) between the light source activated when the individual engages the input device and the light source at the predetermined position may be used as a measure of the accuracy of an individual's anticipation timing. Further, in embodiments, the anticipation-testing system may comprise a recording device to, at least temporarily, store which light source was activated when the individual engaged the input device and/or how temporally accurate the individual's input was. In instances, the recording device may store other information related to testing, evaluation, or user perception(s).

BRIEF DESCRIPTION OF THE SEVERAL VIEWS OF THE DRAWINGS

The present invention is described in detail below with reference to the attached drawing figures, wherein.

DETAILED DESCRIPTION OF THE INVENTION

Figure 1:
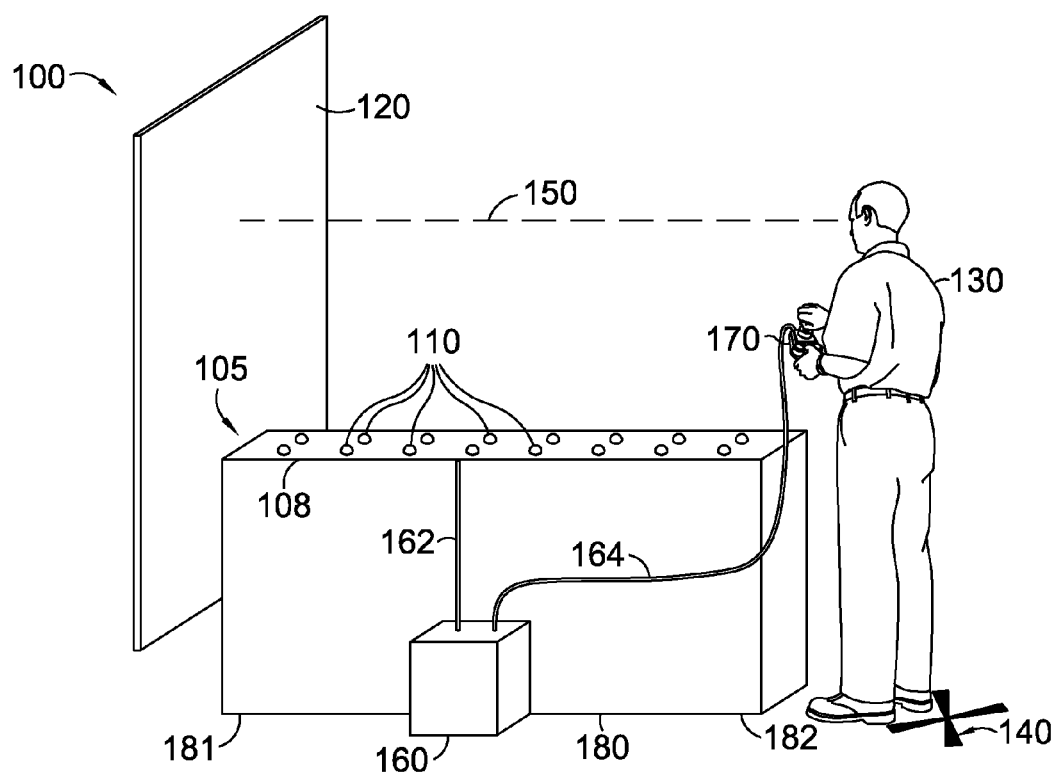
FIG. 1 illustrates an exemplary motion-simulating device depicting a compact, longitudinally aligned beam for accommodating a plurality of light sources, in accordance with an embodiment of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies.

Embodiments of the invention provide an anticipatory-testing system and/or a motion-simulating device for evaluating and/or training the anticipatory abilities (e.g., visual, cognitive, physical, and the like) of an individual. By way of example only and not limitation, a suitable motion-simulating device may include a reflecting surface and a beam that accommodates a plurality of light sources capable of alternating between an active condition and an idle condition. The motion-simulating device may also accommodate a plurality of occlusion features that blocks light emitted from each of the plurality of light sources. The plurality of light sources may be organized into a first plurality of light sources and a second plurality of light sources such that light from the first plurality of light sources is directly viewable by the individual while light emitted by the first plurality of light sources in a direction of the reflecting surface is blocked by the plurality of occlusion features. Conversely, light from the second plurality of light sources is indirectly viewable by the individual via the reflecting surface, but, light emitted in the direction of the individual by the second plurality of light sources is blocked by the plurality of occlusion features. Of course, additional pluralities of light sources whether occluded or directly viewable, may be used in addition to the first plurality of light sources and the second plurality of light sources more particularly described herein.

In an exemplary embodiment, the anticipatory testing/training system further includes a control unit for activating the plurality of light sources in a temporal pattern to create the appearance of movement of a light, and an input device to be engaged by the individual to indicate when the individual perceives a light source at a predetermined position is activated during movement of the light. In one instance, activating in a temporal pattern may include the controller recursively triggering each of the plurality of light sources in a sequential order. In addition, recursively triggering may involve inducing each of the plurality of light sources to cycle through the active condition, typically in a rapid manner.

When testing the anticipation timing of the individual with the motion-simulating device, the reflecting surface may be strategically positioned in an angular orientation with respect to the motion-simulating device such that, during activation in a temporal pattern, the individual perceives the simulated movement of light as originating from a distal location and moving toward a proximal location. Upon perceiving the movement of light as encountering the predetermined position, the individual is prompted to engage the input device. In some embodiments, a recording device may be incorporated in the reaction-testing system to capture which light source was activated when the input device was engaged. Optionally, before providing feedback to the individual, the individual may provide an evaluation of her or his performance. For example, the individual may indicate that she/he was "early," "late," or "on time" in engaging the input device, and then feedback may be provided to the individual. Further, the individual's evaluation may be at least somewhat quantitative, such as "very late," "earlier than last time," etc. Additionally, feedback may be offered to the individual by activating, for a predetermined amount of time, the light source that was activated when the input device was engaged. Although described in one embodiment as capturing information related to which light source was activated and when, the recording device may capture and/or store various other types of information related to testing, evaluation, and user perception(s).

Having briefly described an embodiment of the present invention, an exemplary operating environment for the present invention is described below.

Embodiments of the invention may be described in the general context of a motion-simulating device that functions according to computer code or machine-useable instructions (e.g., test instructions), including computer-executable instructions such as program components, being executed by a computing device (e.g., control unit, input device, or recording device) or other logic-processing machine, such as a personal data assistant or other handheld device. Generally, program components including routines, programs, objects, components, data structures, and the like, refer to code that performs particular tasks, or implement particular abstract data types. Embodiments of the present invention may be practiced in a variety of system configurations, including hand-held devices, consumer electronics, general-purpose computers, specialty computing devices, etc.

Embodiments of the anticipation-testing system, and the motion-simulating device employed thereby, for exercising eye/hand coordination of an individual will now be described with reference to the accompanying drawings. The drawings and the associated descriptions are provided to illustrate embodiments of the present invention and not to limit the scope thereof. Reference in the specification to an "embodiment" is intended to indicate that a particular feature, structure, or characteristic described in connection with the embodiment is included in at least an embodiment of the invention. Further, the appearance of the phrase "in one embodiment" in various places in the specification are not necessarily all referring to the same embodiment.

Figure 6:
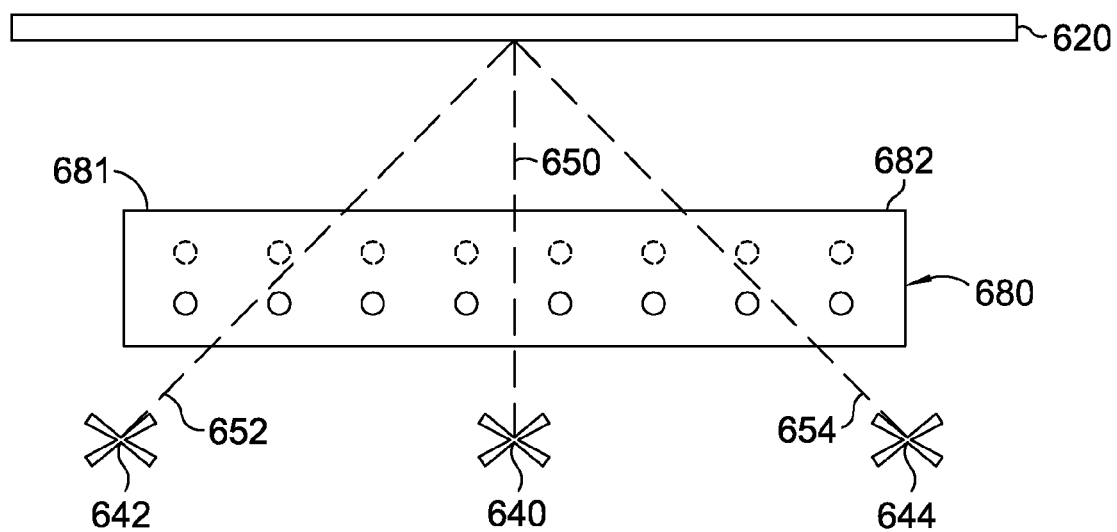
FIG. 6, illustrates a diagrammatic view of a beam in an angular orientation that is lateral with respect to a reflecting surface, in accordance with an embodiment of the present invention.
Figure 7:
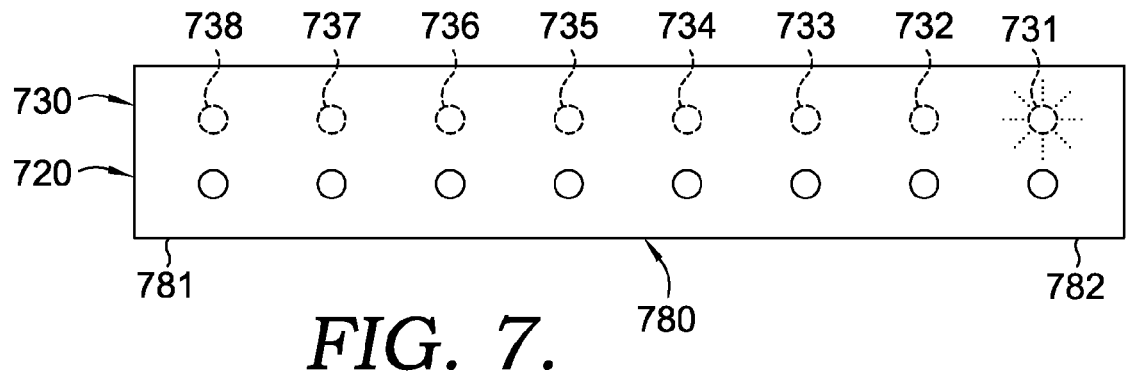
FIGS. 7-10, illustrate diagrammatic views of a plurality of light sources that are sequentially activated to create the appearance of movement of a light, in accordance with an embodiment of the present invention.
Figure 8:
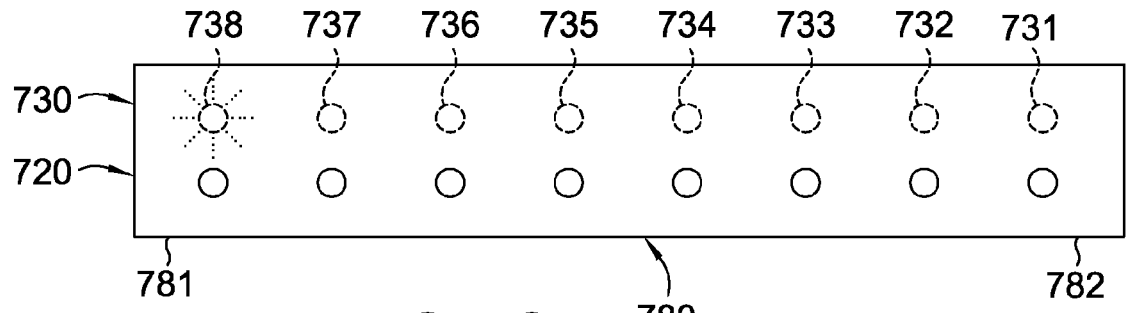

Referring to the drawings in general, and initially to FIG. 1 in particular, a motion-simulating device 105 is shown, in accordance with an embodiment of the present invention. In an exemplary embodiment, the motion-simulating device 105 includes a compact, longitudinally aligned beam 180 for accommodating a plurality of light sources 110, a control unit 160, and an input device 170. The motion-simulating device 105 may be arranged substantially between an individual 130 being tested, and at least one reflecting surface 120. In a specific arrangement, the individual 130 may be located at a first position 140 that is proximate to a second end 182 of the beam 180, and the reflecting surface 120 may be located at a first end 181 of the beam 180. As such, the beam 180 longitudinally extends between the reflecting surface 120 and the first position 140 along a first line of vision 150 of the individual 130. Although one configuration of the beam 180 with respect to the reflecting surface 120 has been shown, it should be understood and appreciated by those of ordinary skill in the art that other angular orientations between the beam 180 and the reflecting surface 120 could be used (e.g., extending laterally between the first position 140 and the reflecting surface 120 as indicated at FIG. 6), and that the invention is not limited to those angular orientations shown and described.

Generally, the beam 180 may be a supportive structure that supports the plurality of light sources 110, for example above an underlying surface. The beam 180 may support the plurality of light sources 110 such that light emitted thereby is exposed to either the individual 130, the reflecting surface 120, or both. In embodiments, the beam 180 may be an elongated rigid member that may be positioned at various angular orientations with respect to the reflecting surface 120. In other embodiments, the beam 180 includes an upper surface 108 on which the plurality of light sources 110 are accommodated. Further, dimensions of the upper surface 108 are configured so that the plurality of light sources 110 may be accommodated in a particular mounting pattern.

Although several embodiments of the beam 180 are described above, various other configurations of the beam 180 and the mounting pattern may be employed. For instance, light sources 110 may be located at any position on beam 180. Further, the beam 180 may comprise several distinct or connected members (e.g., formed a V-shaped component with lights supported on either the sides, the tops, or bottoms of the members of the V-shaped component). Also, the reflecting surface 120 may be positioned at various locations and biased at various angles in relation to the beam 180 (e.g., a minor placed adjacent to the V-shaped component at a lateral relationship, at the point of the V-shaped component, etc.). Further, a reflecting surface having a non-planar surface may be used to magnify, reduce, or otherwise alter the appearance of a light source reflected by the surface. Properties of the light sources and/or reflecting surface may vary, which may be used to further test, and/or train the perception and processing abilities of an individual. For example, an anticipatory response might be appropriate for green light sources, while no response might be appropriate for red light sources. Also, reflecting surfaces may be changed between testing/training sessions, or even during a testing/training-session. For example, various minors with differently contoured surfaces may be rotated to alter the magnification of the reflected image while various light sources are sequentially activated as described herein. Further, the light sources and reflecting surface(s) may be arranged in various configurations relative to one another and/or the individual undergoing testing/training. Various configurations may be used, for example, to test/train the visual ability of an individual for improved performance in a variety of activities. For example, batting in baseball or softball would correspond a first configuration, returning a tennis serve would correspond to a second configuration skeet shooting would correspond to a third configuration, etc.

Some of the various mounting patterns considered by embodiments of the present invention of the plurality of light sources 110, and occlusion features (see reference numeral 230 of FIG. 2) are discussed more fully below with reference to FIGS. 2-4. The plurality of light sources 110 may be accommodated on the beam 180 in a mounting pattern by any manner know to those of ordinary skill in the art. For instance, the plurality of light sources may be secured to the beam 180 in a mounting pattern by adhesives, magnetic technology, mounting hardware, and/or other affixation mechanisms to facilitate attachment at various locations within the mounting pattern. Light sources may be mounted so as to simulate various types of movement, such as linear, curving, zig-zagging, etc. Also, the pace at which light sources are activated and/or deactivated may be varied during a single testing/training-session to simulate an object speeding up or slowing down.

Figure 5:
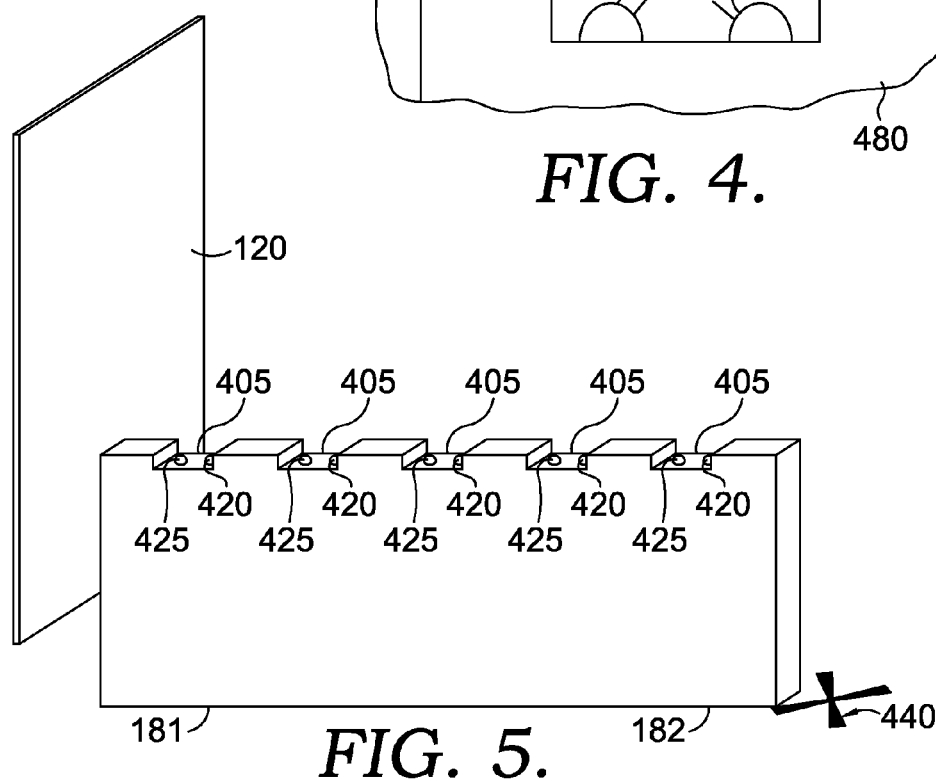
FIG. 5, illustrates a perspective view of the mounting pattern of FIG. 4 applied to a beam of a motion-simulating device, in accordance with an embodiment of the present invention.

Generally, the plurality of light sources 110 may be accommodated on the beam 180 in a mounting pattern between the first end 181 to the second end 182. By way of example, accommodating may include recursively positioning each of the plurality of light sources 110 in pairs according to the mounting pattern. The pairs of light sources may be laterally offset (e.g., as shown in FIG. 1) or longitudinally offset (e.g., as shown in FIG. 5). In one instance, some of the plurality of light sources 110 may belong to a first plurality of light sources, while others of the plurality of light sources 110 may belong to one of a second plurality of light sources. As such, these pairs may include a light source from each of the first and second plurality of light sources, as discussed more fully with reference to FIGS. 2 and 5. Further pluralities of light sources may, of course, also be used in accordance with the present invention. For example, four (or more, or fewer) pluralities of light sources may be provided, with each plurality providing a unique visual characteristic, such as color, trajectory, spacing, etc. Alternatively, individual light sources may possess multiple characteristics, each of which may be activated individually.

Generally, the plurality of light sources 110 may be designed to emit light upon being activated by the control unit 160. The plurality of light sources may include one or more of the following embodiments: a florescent light; an incandescent light; a light-emitting diode (LED); an LCD or other type of display; a laser; an electroluminescent light source; a chemical light; a halogen light; or a flexible light wire. However, the plurality of light sources 110 may be any light source that can produce a pulse/flash light effect when electrically controlled by a control unit 160.

If the plurality of light sources 110 are LCDs or other display devices, a variety of secondary visual characteristics may be incorporated into an activated light source. Such secondary visual characteristics may be incorporated into testing and/or training in accordance with the present invention. For example, an LCD or other display may generate different colors, with different colors requiring different responses from an individual. By way of further example, an LCD or other display device may display an indicia possessing visual details, such as orientation (such as a Landolt C with an orientation of up, down, left or right), rotation (such as an image of a baseball that may spin in a given direction), identity (such as different types of sporting equipment), and the like. The visual details of a displayed indicia may indicate what, if any, response is appropriate from a subject (for example, a button should be pressed when a football indicia reaches a certain point, but no response should be made to baseball indicia). Alternatively, at least one visual detail of a displayed indicia may in combination with other factors, whether circumstances requiring a particular response will be met. For example, the displayed indicia may be a baseball possessing visual traits of rotation, lateral trajectory, and speed. In this example, a subject may be required to depress a button when the indicia reaches a predetermined point (i.e, when the "ball" reaches the "plate"), but only if the indicia is within a predetermined lateral region (i.e., only if the ball is a "strike"). In this example, the visual traits of rotation, lateral trajectory, and speed at the beginning of the motion simulation may be used to predict when and where laterally the indicia will reach the predetermined point. Of course, other visual indicia and visual traits may be used in accordance with the present invention.

In an exemplary embodiment, each of the plurality of light sources 110 are capable of alternating between an active condition and an idle condition. Of course, in other embodiments, such as embodiments using LCDs or other displays, light sources 110 may possess additional visual traits beyond simply active and idle. Typically, the active condition is invoked upon control unit 160 electrically triggering a selected light source, of the plurality of light sources 110, to emit light. Electrically triggering may accomplished by providing a signal to a power supply to supply electricity to the selected light source, providing electricity directly to the selected light source, controlling a switch at the selected light source, or any other method for activating a light source know to those having ordinary skill in the relevant field. The idle condition is invoked by withholding power from the selected light source, thereby causing the selected light source to cease emitting light. Further, the reflecting surface 120 may be non-planar (for example, concave or convex) to create various visual effects. Yet further, the reflecting surface 120 and its reflective properties may be changed or varied to change visual properties as part of testing and/or training in accordance with the present invention.

The reflecting surface 120 may be a mirror or any other reflective material capable providing light emitted from one or more of the plurality of light sources 110 to the individual 130. Embodiments of the reflecting surface 120 may include any element or device capable of reproducing an image (e.g., monitor to display a plurality of light sources as filmed from a certain perspective so as to generally mimic a reflection). In embodiments, the reflecting surface 120 may be repositionable so that the angular orientation between the reflecting surface 120 and the beam 180 may vary without adjusting the beam 180. Accordingly, the reflecting surface 120 may be strategically placed to generate a visual perspective of distance within a limited spatial area.

With continued reference to FIG. 1, the control unit 160 will now be discussed. Generally, the control unit 160 is configured to provide for testing and/or training of the reactionary ability of the individual 130. It will be understood and appreciated by those of ordinary skill in the art that the control unit 160 is merely an example of one suitable computing device and is not intended to suggest any limitation as to the scope of use or functionality of embodiments of the present invention. Accordingly, the control unit 160 may take the form of various types of processors that are commonly deployed in a personal computing device, a handheld device, a consumer electronic device, and the like. It should be noted, however, that embodiments of the present invention are not limited to implementation on any particular processing components.

In an exemplary embodiment, the control unit 160 is generally configured to be any type of microprocessor that is capable of executing test instructions. By way of example only and not limitation, executing test instructions may include activating one or more of the plurality of light sources 110 in a temporal pattern. Control unit 160 may also control any addition visual characteristics, such as color, orientation, rotation, trajectory, etc., (if present in a given embodiment). In one instance, activating in a temporal pattern may involve, but is not limited to, the following process: selecting a light source of the plurality of light sources 110, electrically triggering the selected light source to cycle to the active condition, maintaining the light source in a the active condition for a predetermined amount of time (e.g., millisecond to minutes), and deactivating the selected light source by retuning it to the idle condition. Generally, the processes is repeated numerous times as the control unit 160 selects other light sources to cycle through the active condition.

Although, electrically triggering is described as activating a selected light source individually, electrically triggering may be practiced by activating more than one light sources in conjunction (e.g., simultaneously, in an overlapping manner, additively).

In another instance, activating in a temporal pattern may involve recursively selecting light sources and activating the selected light sources in a sequential manner. As such, "sequential activation" causes one or more light sources of the plurality of light sources 110 to cycle through the active condition individually in an order that simulates motion. One embodiment of simulating motion is more fully described with reference to FIGS. 7-10. Typically, the scheme of the sequential activation, which influences the manner in which motion is simulated, is provided to the control unit 160 as test instructions. Generally, as used herein, the phrase "test instructions" is not meant to be limiting but may embrace all types of code, rules, heuristics, logic, etc., which govern such aspects as which light sources to select, the predetermined time of remaining in the active condition, and generally which temporal pattern to follow when sequentially activating the plurality of light sources 110. Accordingly, upon executing the test instructions, the control unit 160 is capable of controlling the light emitted from each of the plurality of light sources 110. The test instructions may, for example, be generated by control unit 160 in response to parameters entered by a user, such as a coach, physician, trainer, or other individual, or randomly or pseudo-randomly generated by control unit 160. Parameters may be, for example, visual traits possessed by the generated light (particularly if the lights are indicia displayed on LCDs or other display devices).

Typically, a power source (not shown) may be electrically connected to the control unit 160 and/or the plurality of light sources 110. As such, the power source assists in supporting operation of some or all of the electrically-driven components. In embodiments, the power source may be a battery, electrical outlet, power cell, solar panel, or any other source of consistent electrical current.

In one instance, an electrical current provided from the power source is controlled by the control unit 160 and conveyed to the plurality of light sources 110 via a communicative connection 162. In another instance, the communicative connection 162 serves to convey a signal from the control unit 160 to the plurality of light sources 110 to activate or deactivate one or more selected light sources. Similarly, a communicative connection 164 operably couples the control unit 160 to the input device 170. In this way, the communicative couple 164 allows the input device 170 to convey individual-initiated indications to the control unit 160 and/or control signals from the control unit 160 to the input device 170.

In embodiments, the communicative connections 162 and 164 may be may be wired or wireless. Examples of particular wired embodiments, within the scope of the present invention, include USB connections and cable connections. Examples of particular wireless embodiments, within the scope of the present invention, include a near-range wireless network and radio-frequency technology. It should be understood and appreciated that the designation of "near-range wireless network" is not meant to be limiting, and should be interpreted broadly to include at least the following technologies: negotiated wireless peripheral (NWP) devices; short-range wireless air interference networks (e.g., wireless personal area network (wPAN), wireless local area network (wLAN), wireless wide area network (wWAN), Bluetooth™, and the like); wireless peer-to-peer communication (e.g., Ultra Wideband); and any protocol that supports wireless communication of data between devices. Additionally, persons familiar with the field of the invention will realize that a near-range wireless network may be practiced by various data-transfer methods (e.g., satellite transmission, telecommunications network, etc.) that are different from the specific illustrated embodiments.

In other embodiments, the motion-simulating device 105 may not be provisioned with a control unit 160. In this instance, the plurality of light sources 110 are wired together in series and/or in parallel with switches or relay components incorporated in the wiring to control the routing and timing of the activation of the plurality of light sources 110. In this way, when power is applied to the plurality of light sources 110, the wiring directs the power to sequentially activate one or more light sources, thereby simulating motion.

Generally, the input device 170 is configured to be engaged by the individual 130 and to convey an indication of the individual-initiated engagement to the control unit 160 for processing. By way of example only, engagement may be in response to the individual 130 perceiving the simulated motion (i.e., generated by the sequential activation of the plurality of light sources 110) encountering a predetermined light source or other prompt. Input device 170 may be, for example, a microphone, joystick, game pad, wireless device, keyboard, keypad, game controller, force plate, eye tracking system, gesture recognition system, touch sensitive screen, and/or any other input-initiating component that provides wired or wireless data to the motion-simulating device 105. Input device 170 may include voice recognition equipment and/or software that processes auditory inputs from the test subject. For example, the auditory input from the subject, in order to show recognition of the visual indicia and/or a visual trait(s) possessed by the visual indicia (for example, if a LCD or other display device is used), may be a verbalization of the trait possessed by the visual indicia. In one embodiment, if the trait is a direction orientation of a Landolt "C," the responsive auditory inputs may be "up," "down," "right," and "left." However, one skilled in the art will understand and appreciate that other auditory inputs may be used (e.g., stating a color, numeral, letter, symbol, etc.) to indicate that the subject perceived and/or recognized the visual indicia. It should be noted, however, that the present invention is not limited to implementation on such input devices 170, but may be implemented on any of a variety of different types of devices within the scope of embodiments hereof. Input indicating the subject's response to a displayed visual indicia may be received and captured with input device 170. If the trait is a directional orientation, a satisfactory test response may be identifying the direction that the visual indicia is facing. By way of example only, without limitation, identifying may include the subject providing input by manipulating a joystick in a direction corresponding to the directional orientation on a hand-held device employed as the input device 170.

If input device 170 is an eye tracking system, the position and/or focus of the eyes of subject may be monitored and an input registered when the eyes are positioned and/or focused at the proper location.

Input devices may also mimic the equipment used in any activity of interest for the individual participating in the testing/training in accordance with the present invention. For example, a baseball bat may be swung by a baseball player at the time the player believes the activated light source (such as, but not limited to, an indicia depicting a baseball displayed on a light sources comprising LCDs) reaches a predetermined location. Similarly, tennis rackets, baseball gloves, hockey sticks (field or ice), lacross sticks, croquet mallets, or any other type of equipment used in an activity, particularly sports, may be used. Inertial sensors may be used in conjunction with actual or simulated equipment. Any other detection method may be used, however, such as motion tracking systems of any kind, detectors that activate when a beam (such as a laser) is interrupted, proximity detectors, and the like.

If input device 170 is a gesture recognition system, a variety of systems and/or methods may be used to receive inputs. For example, one or more cameras may be used to monitor the movement of a subject's body limbs and/or extremities and, in conjunction with appropriate hardware and/or software, register an input when subject makes an appropriate gesture. Gesture recognition systems may also utilize optical markers attached to subject to facilitate motion tracking. Transmitters attached to subject and receivers (for example, utilizing radio infrared, sonic, subsonic, or ultrasonic transmissions) may also be utilized as part of a gesture recognition system.

If input device 170 is a touch sensitive screen, any type of touch sensitive screen may be utilized. Also, an overlay of a touch sensitive material may be used to receive touch inputs in conjunction with a display that is not itself touch sensitive. Such an overlay may be any distance from the display.

Further, a secondary or other additional input may be received by input devices 170 or additional input device(s) (not shown). A secondary or other additional input may comprise, for example, an indication of whether a subject believes she/he was "early," "late," or "on time." A secondary or other additional input may also comprise, for example, an identification of a visual characteristic possessed by an indicia, such as orientation, color, rotation, etc.

Although not shown, a recording device may be incorporated within the motion-simulating device 105. In one instance, the recording device is an external piece of equipment is operably coupled to control unit 160 via a communicative connection. In another instance, the recording device is a data-storage component integrated within the control unit 160. In operation, the recording device is configured to retain information such as an activation time of the input device 170, an activation time of the predetermined light source, which light source was activated during the activation time, test instructions, test data, and the like. This information may be searchable at the recording device by the control unit 160 or any other computing device. Further, the information may downloadable from the recording device to perform analysis thereof, such as calculating a time period that elapsed between the activation time and the activation time. Further yet, information (e.g., test instructions) may be unloadable to the recording device such that it is accessible to the control unit 160. Although various embodiments of information are discussed above, the content and volume of such information is not intended to limit the scope of embodiments of the present invention in any way.

In one embodiment of operation, as shown in FIG. 1, the reaction-testing system 100 arranged such that the beam 180 extends longitudinally between the first position 140, where the individual 170 is located, and the reflecting surface 120. As such, the angular orientation of the beam 180 is substantially perpendicular to the reflecting surface 120. Additionally, the beam 180 and the first line of vision 150 reside in substantially perpendicular-spaced relation.

Initially, the control unit 160, executes test instructions to determine which of plurality of light sources 110 to activate. Typically, the test instructions provide a temporal pattern that governs the activation. As discussed above, the temporal pattern may indicate that the plurality of light sources 110 are to be sequentially activated to create the appearance of movement of a light, or simulated motion. Such simulated motion may include additional characteristics, such as changing speed or pace, and may further include characteristics such as color, orientation, rotation, etc. During execution of the test instructions, the control unit 160 recursively triggers one or more of the plurality of light sources 110, via communicative connection 162, to cycle through the active condition. In this way, the control unit 160 causes the plurality of light sources 110 to express the temporal pattern to the individual 130. In an exemplary embodiment, the control unit 160 initially sequentially activates light sources, within the plurality of light sources 110, that are indirectly viewable from the individual 130 in the first position 140. As such, the individual 130 perceives light emitted from the indirectly viewable light sources through the reflecting surface 120 along the first line of vision 150. Next, the control unit 160 initially sequentially activates light sources, within the plurality of light sources 110, that are directly viewable from the individual 130 in the first position 140. As such, the individual 130 perceives light emitted from the directly viewable light sources directly from their position on the beam 180, and not through the reflecting surface 120. In this way, sequential activation of the indirectly viewable light sources then the directly viewable light sources in the temporal pattern effectively creates the appearance of a light originating from a distal location, with respect to the individual 130, and moving to a proximal location along the first line of vision 150. As described herein, such simulated motion may be used to test and/or train the anticipatory abilities of an individual.

At any time before or during the sequential activation, the individual 130 is prompted to provide a response that tests the individual's anticipatory abilities with regard to a moving light. In one instance, the prompt is a previously established light source located on the beam 180 in a predetermined position. In application, a test is commenced and the moving light, as simulated by the sequential activation, begins encroaching on the predetermined position. At this point, the individual 130 may be anticipating the timing of when the moving light will reach the predetermined position. Based on this anticipation of movement of the light, the individual 130 may attempt to provide an indication concurrently with the moving light arriving at the predetermined position. In one instance, the individual 130 may indicate (e.g., individual-initiated activation) when he or she believes the light will reach the predetermined position using or engaging the input device 170.

Upon engagement, the input device 170 transmits an input (e.g., created by the indication of the activation) via the communicative connection 164, to the control unit 160. The control unit 160 may determine an activation time based on the indication. In addition, the control unit 160 may know, or have access to at the recording device, an expected response. The expected response may include such information as the activation time of the light source in the predetermined position.

In embodiments, the control unit 160 may function as an analytical processor to evaluate the reactionary ability of the individual 130. Evaluation may be performed by comparing the response from the individual 130 to the expected response. In one instance, comparing responses includes comparing the activation time against the time the predetermined position was actually reached by the moving light. Based on the comparison, time period that elapsed between the individual's 130 response and the time the moving light reached the predetermined position may be calculated. In addition, it can be determined whether the individual's 130 response occurred before (i.e., over anticipating) or after (i.e., delayed response) the time the moving light reached the predetermined position.

Further, in embodiments, the control unit 160 may function as a training device by providing feedback to the individual 130. Feedback may be presented in any form and may be based on any information, including unprocessed response times, manipulated test results, and predetermined data from the test instructions. In one instance, the form in which feedback is presented is light emitted from one or more of the plurality of light sources 110, where the control unit 160 electrically triggers the light sources to cycle to the active condition. By way of example only, the control unit 160 may electrically trigger the light source that was activated during the activation time, permitting the individual to determine how "close" he or she was to the correct timing.

Additionally, although a particular configuration of the plurality of light sources 110 has been shown (e.g., manner of operation, mounting pattern, etc.), it should be understood and appreciated by those of ordinary skill in the art that other methods for operating the plurality could be used, and that the invention is not limited to the embodiments shown and described. For instance, an intensity of the electrical current used to activate the plurality of light sources 110 may be modulated to generate variable strengths of light emitted therefrom. When applied during testing, this modulating feature may enhance the appearance of a light moving toward the individual 130 along the first line of vision 150.

In a specific embodiment of operation, the anticipation timing-testing system 100 may be configured to simulate an environment of a baseball game. For instance, the moving light may mimic a pitch to a batter. Accordingly, the individual 130 being tested may act as the batter who is anticipating a pitch. Once the "pitch," simulated by the moving light, arrives at "home plate," simulated by the predetermined position, the individual 130 may attempt to concurrently trigger the input device 170. That is, the individual 130 may attempt to swing a bat or generate a movement that creates an input at the time the moving light reaches the predetermined position.

By way of example, the beam 180 may be designed such that the activation of the pattern of the plurality of light sources 110 may imitate a ball thrown between a pitcher's mound and a batter at home plate, which may be the location of the individual 130 being tested. In addition, the reflective surface 120 allows the beam 180 to be designed considerably shorter than 60 feet, 6 inches, which is the distance between a pitcher's mound and home plate, and yet still simulate a pitch being thrown from that distance. As such, the size of the beam 180 may be scaled upward or downward in relation to the speed of the moving light and a placement of the reflecting surface 120 such that a particular distance and speed may be simulated to the individual 130.

The speed of the moving light may be adjusted to enhance the simulation of the pitch. For instance, the speed of the moving light, as controlled by the control unit 160, may be variable to simulate pitches a different speeds. By controlling the time to respond (e.g., a fastball thrown at 95 mph to an underhand pitch at 5 mph), the anticipation-testing system 100 may test various levels of the individual's anticipatory skills.

The present invention may be used for anticipation timing testing/training with specific application to a variety of activities. For example, anticipation timing related to sports such as soccer, hockey, football, etc. may be tested/trained in accordance with the present invention. In some instances, the predetermined location may be proximate to an individual, while in other instances the predetermined location may be distant from an individual. Further, in some instances the simulated motion may be towards the individual, in other instances the simulated motion may be away from the individual, in yet other instances the simulated motion may be lateral to the individual, and in yet further instances the simulated motion may be at an angle to the individual. For testing/training anticipation timing for some particular activities, such as playing the quarterback position in American football, an individual may attempt to activate a second series of motion simulating light sources so that it will intersect a target motion simulating light sources at a particular location or time, which will require an individual to "lead" the target light sources.

Figure 2:
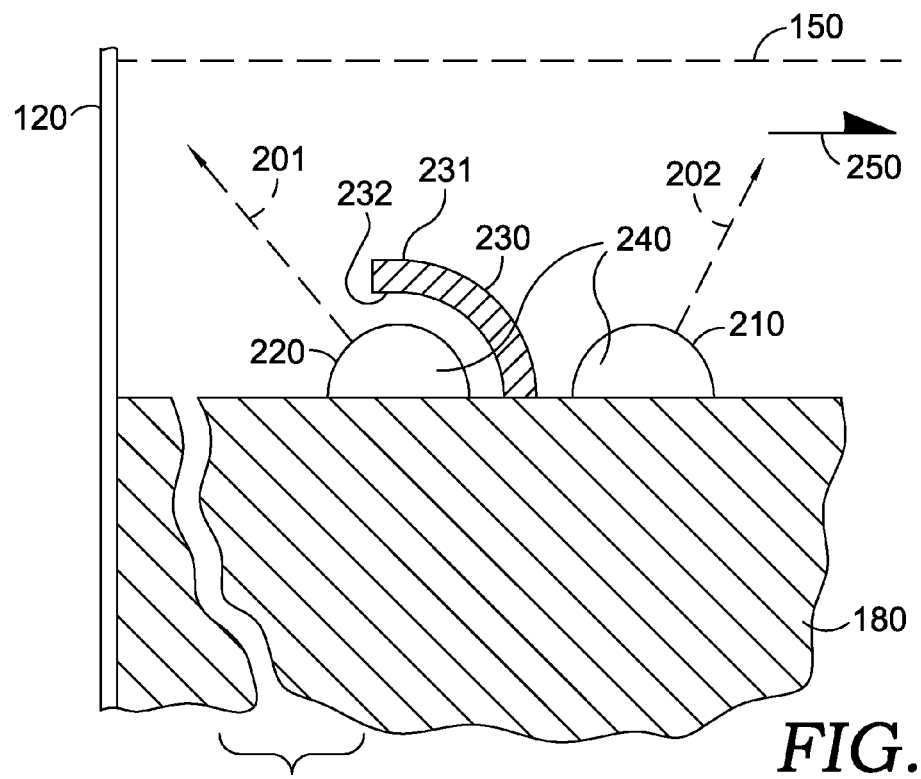
FIG. 2, illustrates a cross-sectional view of a mounting pattern that has a recurring pair of light sources and an occlusion feature, in accordance with an embodiment of the present invention.

Turning now to FIG. 2, a cross-sectional view that illustrates a mounting pattern that has a recurring pair of light sources 240 and an occlusion feature 230 is shown, in accordance with an embodiment of the present invention. In this embodiment of the mounting pattern, the recurring pair of light sources 240, which are included in the plurality of light sources (e.g., reference numeral 110 of FIG. 1) discussed above, include light sources 210 and 220. As configured, the light source 210 emits light 202 that is directly viewable by the individual 250. However, the light 202 emitted from the light source 210 is prevented from directly reaching the reflecting surface 120. Accordingly, the light source 210, and those light source arranged in a similar manner, are considered to be included within the first plurality of light sources (i.e., directly viewable by the individual 250). The light source 220 emits light 201 that is indirectly viewable by the individual 250 because light 201 emitted from the light source 220 is prevented from directly reaching the individual 250 by the occlusion feature 230. However, the light 201 emitted from the light source 220 may reach the reflecting surface 120 directly. Accordingly, the light source 210, and those light source arranged in a similar manner, are considered to be included within the second plurality of light sources (i.e., indirectly viewable by the individual 250 through the reflecting surface 120).

In this embodiment of the mounting pattern depicted in FIG. 2, the occlusion feature is a shoulder-shaped protrusion from the beam 180 that includes a curvature. The curvature is formed such that a concave surface 232 is facing the light source 220 and a convex surface 231 is facing the light source 210. As such the light sources 210 and 220 are arranged adjacent to the occlusion feature 230 and longitudinally-aligned with the first line of vision 150. During sequential activation, the concave surface 232 of the occlusion feature 230 prevents the light 201 emitted from the light source 220 from being directly viewed by the individual 250, but allows light 201 to directly reach the reflecting surface 120. Conversely, the convex surface 231 of the occlusion feature 230 prevents the light 202 emitted from the light source 210 from reaching the reflecting surface 120, but allows light 202 to be directly viewable by the individual 250.

Although formed as a curved protrusion, the occlusion feature 230 may be formed in any manner know in the fabrication industry. For instance, the occlusion feature 230 may be bent at one or more angles. In addition, the embodiment discussed above depicts the light sources 210 and 220 as being longitudinally offset. In other embodiments of the recurring pair of light sources 240, the light sources 210 and 220 may be laterally offset. In this case, the occlusion feature 230 may be an elongated member fixedly attached to the beam 180 between the light sources 210 and 220.

Figure 3:
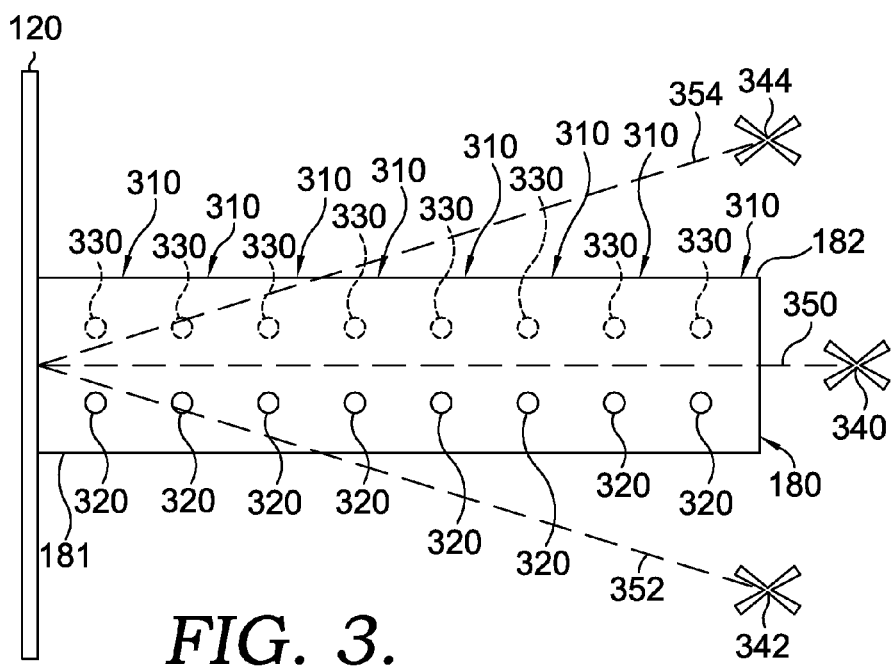
FIG. 3, illustrates a diagrammatic view of various lines of vision each associated with a position that may be occupied by an individual being tested, in accordance with an embodiment of the present invention.

With reference to FIG. 3, a diagrammatic view is illustrated showing of various lines of vision 350, 352, and 354 each associated with a position 340, 342, and 344, respectively, that may be occupied by an individual being tested, in accordance with an embodiment of the present invention. Generally, the positions include a first position 340 that is associated with a first line of vision 350, a second position 342 that is associate with a second line of vision 352, and a third position 344 that is associated with a third line of vision 354. The beam 180 is angularly oriented with respect to the reflecting surface 120 such that it extends longitudinally between the first position 340 and the reflecting surface 120. In particular, the positions 340, 342, and 344 are located adjacent to the second end 182 of the beam 180, while the reflecting surface 120 is located adjacent to, or adjoining, the first end 181 of the beam 180. The beam 180 also accommodates a plurality of recurring pairs of light sources thereon, where each pair of light sources includes a light source 320 that is directly viewable by an individual located in one of the positions 340, 342, or 344, and a light source 330 that is indirectly viewable by the individual through the reflecting surface 120. As such, the light sources 320 comprise the first plurality of light sources, while the light sources 330 comprise the second plurality of light sources.

During testing, one or more individuals may be located at the positions 340, 342, and/or 344. Accordingly, the individual(s) are tested from various angular orientations with respect to the beam 180 and reflecting surface 120. In this way, a robust test procedure may be performed to comprehensively evaluate the scope of an individual's visual or peripheral perception.

Figure 4:
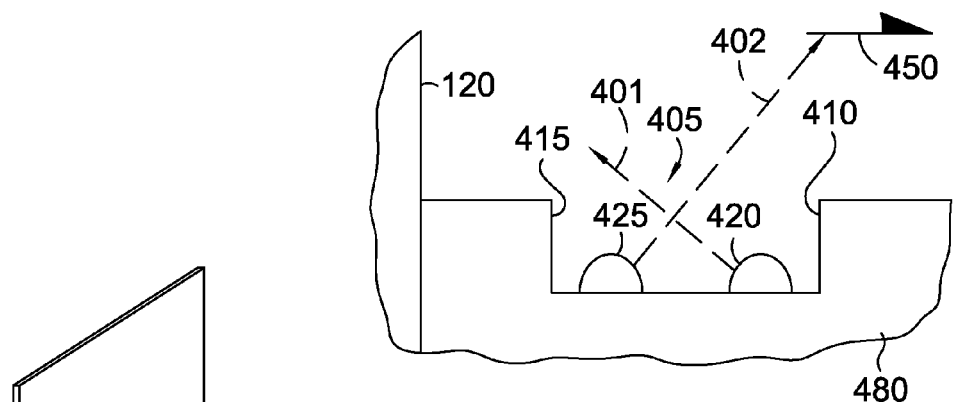
FIG. 4, illustrates an elevation view of a mounting pattern that has a recurring pair of light sources and an occlusion feature, in accordance with an embodiment of the present invention.

Turning to FIG. 4, an elevation view of a mounting pattern is illustrated that shows a recurring pair of light sources and an occlusion feature 405, in accordance with an embodiment of the present invention. The recurring pair of light sources (e.g., reference numeral 240 of FIG. 2) includes a light source 420 and a light source 425 considered to be in the second plurality of light sources and the first plurality of light sources, respectively. In the embodiment depicted, the occlusion feature 405 is generally a depression in a beam 480 in which the light sources 420 and 425 reside in longitudinal-spaced relation. The depression may include a wall 410 that faces the reflecting surface 120 and prevents light 401 emitted from the light source 420 from being directly viewable by an individual 450. However, the light 401 is indirectly viewable by the individual 450 through the reflecting surface 120. In addition, the depression may include a wall 415 that faces the individual 450 and prevents light 402 emitted from the light source 425 from directly reaching the reflecting surface 120, but allows the light 402 to be directly viewable by an individual 450. In this way, when sequentially activating the light sources 420 and 425, the light 401 from the light source 420 appears to be farther away from the individual 450 than the light 402 from the light source 425.

With reference to FIG. 5, a perspective view of the mounting pattern of FIG. 4 applied to the beam 480 of a motion-simulating device is shown, in accordance with an embodiment of the present invention. In this embodiment, each pair of the light sources 420 and 425 are associated with, and reside within, each of the occlusion features 405. During testing, those light sources 420 appear distal to an individual located at position 440, as the light emitted therefrom typically reflects off of the reflecting surface 120 before reaching the individual, i.e., a longer path to travel. Conversely, the light sources 425 appear proximal to the individual as the light emitted therefrom travels less distance. More specifically, those light sources 420 arranged proximate to the second end 182 of the beam appear furthest away from the individual, while those light sources 425 arranged proximate to the second end 182 of the beam appear closest to the individual. Accordingly, a temporal pattern that includes sequential activation commencing with the light sources 420 at the second end 182, then the light sources 420 at the first end 181, then the light sources 425 at the first end 181, an concluding at the light sources 425 at the second end 182 simulate motion to an individual located at the position 440. In particular, the simulated motion replicates a light moving toward the individual along a vector aligned with the beam.

Turning now to FIG. 6, a diagrammatic view of a beam 680 in an angular orientation that is lateral with respect to a reflecting surface 620 is shown and will be discussed below, in accordance with an embodiment of the present invention. Similar to FIG. 3, various positions are shown. Generally, the positions include a first position 640 that is associated with a first line of vision 650, a second position 642 that is associate with a second line of vision 652, and a third position 644 that is associated with a third line of vision 654. The beam 680 is angularly oriented with respect to the reflecting surface 120 such that it extends longitudinally between the first position 640 and the reflecting surface 120. In particular, the positions 640, 642, and 644 are opposed from the reflecting surface 620 across the beam 680. In this orientation, the plurality of light sources may sequentially activate laterally in a consecutive pattern between ends 681 and 682 of the beam 680. That is, the beam 680 accommodates the plurality of light sources thereon, such that the sequential activation creates the appearance of motion of a light that is substantially perpendicular to the first line of vision 640, and that is in an angular vector with respected to second line of vision 642 and third line of vision 644. As such, the simulated motion may test the reactionary ability of an individual by focusing on specific portions of a reactionary response (e.g., test perception of a left eye and of a right eye in general isolation).

With reference to FIGS. 7-10, diagrammatic views of a plurality of light sources that are sequentially activated to create the appearance of movement of a light are shown and will be discussed together, in accordance with an embodiment of the present invention. Generally, light sources 731-738 and 721 and 728 are accommodated on a beam 780, where the light sources 731-738 are considered to comprise a second plurality of light sources 730 that are indirectly viewable to the individual, while the light sources 721-728 are considered to comprise a first plurality of light sources 720 and are directly viewable by the individual. Although not graphically depicted, the individual is located proximate to end 782 of the beam 788 and a reflecting surface is located adjoining, or adjacent to, end 781 of the beam 788.

Figure 9:
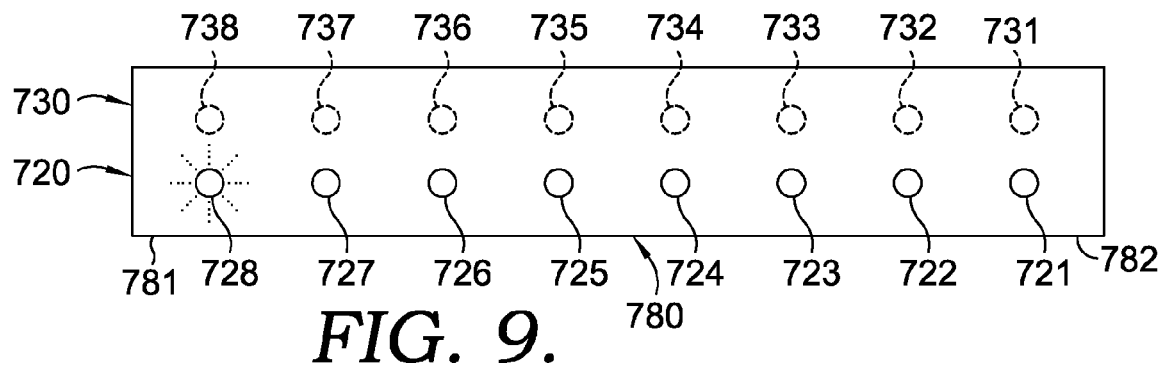
Figure 10:
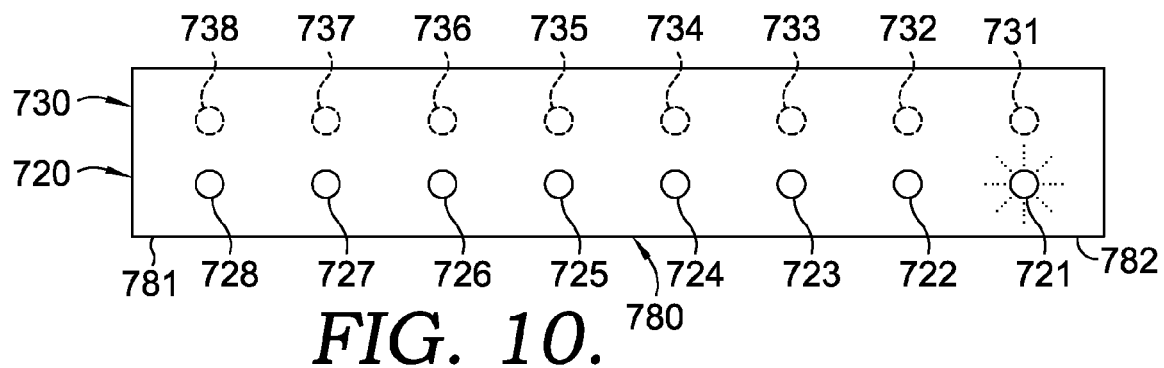

An embodiment of sequential activation that creates the appearance of light moving toward the individual will now be discussed. Initially, light source 731 is activated (e.g., cycled through the active condition) to create emitted light that is indirectly viewable to the individual through the reflecting surface. The light sources 732-738 are then sequentially activated in a consecutive manner away from the individual from the end 782 to the end 781. The light source 738 is depicted activated in FIG. 8. Next, as depicted in FIG. 9, the light source 782 is activated, which is the first light source of the first plurality of light sources 720 to be activated in this embodiment of the sequential activation. The light sources 721-727 are then sequentially activated in a consecutive manner toward from the individual from the end 781 to the end 782. In this way, this procedure of sequential activation shown in FIGS. 7-10 creates the appearance of a light originating from a distal location and moving, either slowly or rapidly, to a proximal location, as perceived by the individual.

Figure 11:
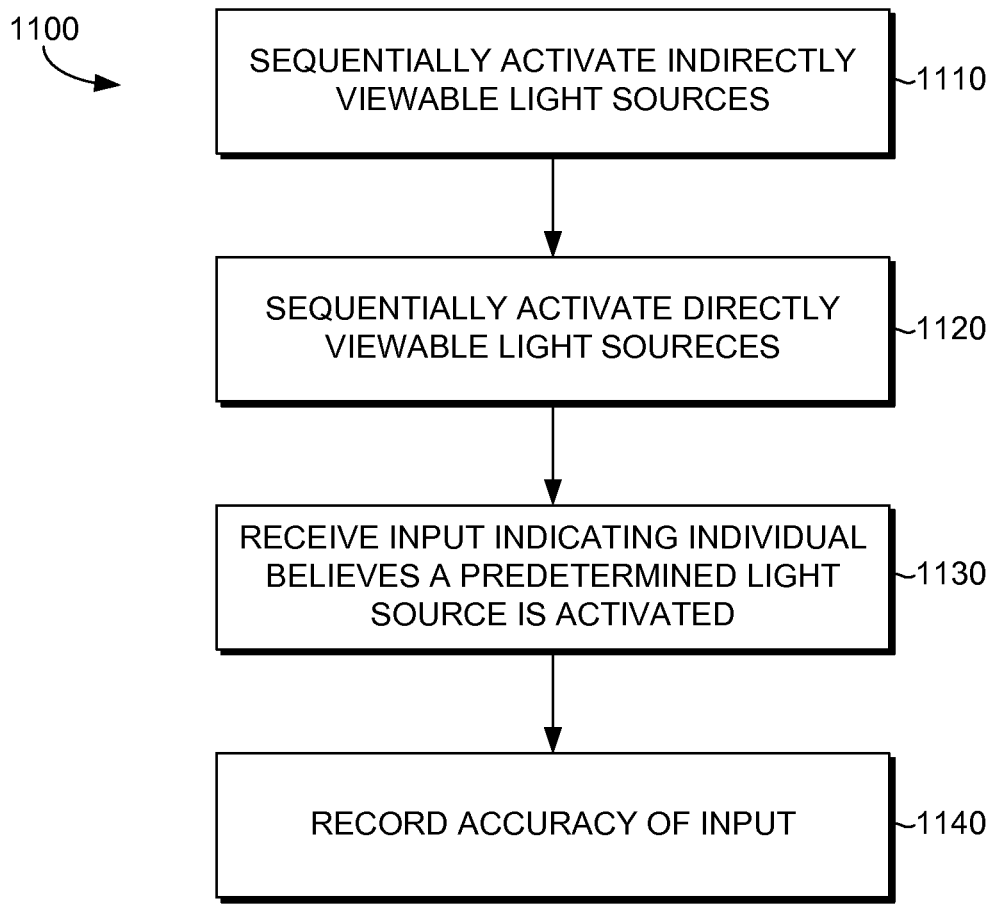
FIG. 11 is a flow diagram showing a method for testing and/or training an individual utilizing a motion-simulating device, in accordance with an embodiment of the present invention.

With reference to FIG. 11, a flow diagram is illustrated that shows a method 1100 for testing and/or training an individual utilizing a motion-simulating device, in accordance with an embodiment of the present invention. As depicted at block 1110, the indirectly viewable light sources are sequentially activated. As discussed above, these light sources may be viewable a reflection in a reflecting surface. As indicated at block 1120, the directly viewable light sources are sequentially activated. By activating the light sources in this manner, the reflecting surface may generate a visual perspective of distance within a limited spatial area, thereby allowing the motion-simulating device that houses the light sources to be compact in size. Of course, block 1110 and block 1120 may occur in any order is simulate motion indifferent directions. As indicated at block 1130, an input indicating that an individual believes a predetermined light source is activated is received. Optionally, an individual may also indicate after their input whether they believe they were early/late/on-time, etc. Based on the received input, the accuracy of the input with respect to an expected response is evaluated and recorded, as indicated at block 1140.

Although depicted as a particular temporal pattern, various visually distinct temporal patterns may be expressed by the plurality of light sources, as controlled by the control unit. These temporal patterns may be expressed upon the control unit executing one or more test instructions, or may be pre-programmed into the control unit. Further, these temporal patterns may include any form of sequential activation of the plurality of light sources, which may or may not create the appearance of a light moving. Even further, sequential activation may be any activation that causes one or more light sources to pulse, flash, illuminate for a fixed period of time at a particular color and intensity.

The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and sub-combinations are of utility and may be employed without reference to other features and sub-combinations. This is contemplated by and is within the scope of the claims.

The invention claimed is:

1. A motion-simulating device that simulates motion to an individual viewing the motion-simulating device from a first position relative to the motion-simulating device, the motion-simulating device comprising:
   at least one reflecting surface viewable from the first position;
   a first plurality of light sources directly viewable from the first position;
   a second plurality of light sources longitudinally offset from the first plurality of light sources, the second plurality of light sources indirectly viewable from the first position using the at least one reflecting surface; and
   a beam that holds the first plurality of light sources and the second plurality of light sources between the at least one reflecting surface and the first position,
   wherein the light sources in the first plurality of light sources and the second plurality of light sources activate in a temporal pattern to create the appearance of movement of a light from the first position.

2. The motion-simulating device of claim 1, wherein the first plurality of light sources are not indirectly viewable from the first position using the at least one reflecting surface.

3. The motion-simulating device of claim 1, wherein the second plurality of light sources are not directly viewable from the first position.

4. The motion-simulating device of claim 1, wherein only one light source of the first plurality of light sources and the second plurality of light sources is activated at any given time.

5. The motion-simulating device of claim 4, wherein:
the first plurality of light sources are not indirectly viewable from the first position using the at least one reflecting surface; and
the second plurality of light sources are not directly viewable from the first position.

6. The motion-simulating device of claim 5, wherein the at least one reflecting surface comprises a mirror.

7. The motion-simulating device of claim 5, wherein:
the first plurality of light sources comprise display devices that display indicia having at least one visual characteristic; and
the second plurality of light sources comprise display devices that display indicia having at least one visual characteristic.

8. The motion-simulating device of claim 5, wherein the beam extends longitudinally between the at least one reflecting surface and the first position.

9. The motion-simulating device of claim 5, wherein the beam extends laterally between the at least one reflecting surface and the first position.

10. The motion-simulating device of claim 1, further comprising:
an input device to be engaged by the individual at the first position to indicate when the individual believes that light at a predetermined position is activated.

11. The motion-simulating device of claim 10, further comprising:
a secondary input device that receives an input from the individual indicating whether the individual believes they engaged the input device before, after, or while light at a predetermined position was activated.

12. The motion-simulating device of claim 10, wherein the light source activated when the input device is engaged remains activated for a predetermined period of time.

13. The motion-simulating device of claim 10, further comprising a recording device that records which light source is activated when the input device is engaged.

* * * * *